(12) United States Patent
Lee et al.

(10) Patent No.: US 7,838,257 B2
(45) Date of Patent: Nov. 23, 2010

(54) EVALUATION METHOD OF ORGANIC OR BIO-CONJUGATION ON NANOPARTICLES USING IMAGING OF TIME-OF-FLIGHT SECONDARY ION MASS SPECTROMETRY

(75) Inventors: Tea Geol Lee, Daejeon (KR); Hyegeun Min, Daejeon (KR); Dae Won Moon, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 303 days.

(21) Appl. No.: 12/149,223

(22) Filed: Apr. 29, 2008

(65) Prior Publication Data
US 2009/0148862 A1     Jun. 11, 2009

(30) Foreign Application Priority Data
Dec. 11, 2007   (KR) ...................... 10-2007-0128074

(51) Int. Cl.
G01N 33/53    (2006.01)
G01N 33/543   (2006.01)
(52) U.S. Cl. ...................... 435/7.21; 435/7.1; 436/501; 436/518; 422/50; 422/60; 424/9.1
(58) Field of Classification Search ........................ None
See application file for complete search history.

(56) References Cited

U.S. PATENT DOCUMENTS

2007/0249060 A1    10/2007 Kirschner et al.

FOREIGN PATENT DOCUMENTS

| JP | 7-153808 | 6/1995 |
| JP | 2004-251623 | 9/2004 |
| KR | 10-2005-0106323 | 11/2005 |

OTHER PUBLICATIONS

H Min et al., "Probing Ligands and Biomolecules Conjugated onto Quantum Dots Using Mass Spectrometric Imaging", Biomaterial Interfaces, AVS 54th Intl Symposium, Oct. 14, 2007.

*Primary Examiner*—Lisa V Cook
(74) *Attorney, Agent, or Firm*—Clark & Brody (57) ABSTRACT

A method of evaluating conjugation between materials using imaging of time-of-flight secondary ion mass spectrometry (TOF-SIMS) according to the present invention is carried out by following the steps, a) forming a spontaneous pattern on a substrate with a mixture containing nanoparticles and a conjugation material selected from organic, bio or inorganic material, b) obtaining an ion detection pattern from the conjugation material and nanoparticles, respectively, depending on their position on the substrate by using time-of-flight secondary ion mass spectrometry, and c) determining whether the conjugation is formed between the conjugation material and nanoparticles by comparing the ion detection pattern of the conjugation material with the ion detection pattern of the nanoparticles.

15 Claims, 5 Drawing Sheets

EVALUATION METHOD OF ORGANIC OR BIO-CONJUGATION ON NANOPARTICLES USING IMAGING OF TIME-OF-FLIGHT SECONDARY ION MASS SPECTROMETRY

TECHNICAL FIELD

The present invention relates to a method of evaluating conjugation between organic and inorganic materials, inorganic and inorganic material, organic and organic materials or organic and bio materials that are present on nanoparticles, using imaging of time-of-flight secondary ion mass spectrometry (TOF-SIMS). Further, the present invention relates to an evaluation method by which conjugation level and an amount of conjugated material can be determined both quantitatively and qualitatively.

BACKGROUND

For most analysis based on biochip or nanoparticles, a scanner using laser induced fluorescence is widely used, since a conjugation reaction between DNA and a protein alone cannot provide an electric signal. Thus, for such case, a sample to be determined is first conjugated to a fluorescent material and then reacted with an arrayed biomaterial so that the degree of biochemical reaction can be determined by measuring fluorescence at a conjugation site. However, such fluorescence detection method is disadvantageous in that an expensive laser must be employed and it cannot be applied to an ultrafine array system.

Recently, a detection method using semi-conducting and water-soluble quantum dots such as CdSe, which emits fluorescence, has been developed instead of using fluorescence materials.

In general, a fluorescent material consisting of organic compounds is chemically unstable and its fluorescence activity is induced only when it is excited with laser having specific wavelength. On the other hand, nanoparticles (i.e., quantum dots) can be easily excited without laser so that it requires a rather simple detection instrument. In addition, it has a highly-sensitive analytical power and an excellent light stability and photoluminescence (PL) of which intensity can be adjusted. As such, as a new kind of fluorescent marker in bio-imaging field, nanoparticles are now getting more attention than ever.

Furthermore, since a biosensor using magnetic beads, magnetic nanoparticles or magnetic sensor is small and light, consumes little electricity and can be integrated, a cheap sensor can be reproducibly mass-produced. In addition, it has a high sensitivity and reliability for detecting a sample with extremely small amount. However, a difficulty to produce a complex having conjugation between magnetic nanoparticles and a specific bio-material remains as a problem for its actual application.

Although many studies have been made on synthesis of fluorescent nanoparticles or magnetic nanoparticles, there are only a few studies regarding chemical properties of conjugation between nanoparticles (or quantum dots) and bio-materials such as protein extract, antibody, and nucleotide.

Until now, many efforts have been made to identify a ligand molecule that is conjugated to nanoparticles. Specifically, nuclear magnetic resonance (NMR) spectroscopy, optical spectroscopy, and Fourier transformed infrared spectroscopy (FT-IR), etc. were used to determine the progress of ligand substitution and bio-conjugation. However, such macroscopic analytical methods are not sufficient to identify a ligand which is actually coordinated to nanoparticles, and not suitable to determine the actual amount and the distribution of the conjugation, etc.

According to the present invention, by using TOF-SIMS, especially an imaging technology of TOF-SIMS, a method which allows an evaluation of conjugation between materials, a progress of conjugation reaction, and a quantitative analysis of conjugated materials, is provided.

Secondary ion mass spectrometry (SIMS) has been generally used as a means for obtaining depth profile of a specific impurity or its lateral profile on same surface at production level for preparing semiconductor device, as it is described in Japanese Patent Application Laid-open No. 1995-153808.

Recently, a method of analyzing biological sample by using mass spectrometry, in particular matrix-assisted laser desorption/ionization time-of-flight mass spectrometry (MALDI-TOF), has been described in Korean Patent Application Laid-open No. 2005-0106323, Japanese Patent Application Laid-open No. 2004-251623 and US Patent Application Laid-open No. 2007-0249060, respectively. However, it is used only for analyzing a product obtained after completion of a reaction, and is different from the method of the present invention wherein conjugation between two materials present on nanoparticles is determined based on a measurement result of TOF-SIMS.

DISCLOSURE OF INVENTION

Technical Subject

An object of the present invention is, for solving the above-described problems of prior art, to provide an evaluation method based on TOF-SIMS that can be used for determining the presence or the absence of conjugation between nanoparticles and an organic, bio or inorganic material and a progress of the conjugation reaction, and for a quantitative/qualitative analysis of the kinds and the amount of the conjugated materials.

Another object of the present invention is to provide an evaluation method based on TOF-SIMS that can be used for determining the presence or the absence of conjugation between organic and inorganic materials, inorganic and inorganic material, organic and organic materials or organic and bio materials that are present on nanoparticles, respectively, and a progress of the conjugation reaction, and for a quantitative/qualitative analysis of the kinds and the amount of the conjugated materials.

Still another object of the present invention is to provide an evaluation method based on TOF-SIMS that can be used for determining the presence or the absence of conjugation of nanocomplexes at each step, that are produced by multi-step conjugation or substitution process based on nanoparticles, a progress of the conjugation reaction, and for a quantitative/qualitative analysis of the kinds and the amount of the conjugated materials.

Still another object of the present invention is to provide an evaluation method based on TOF-SIMS that can be used for determining the presence or the absence of conjugation between nanoparticles and functional groups which can form a specific conjugation to a biological subject to be detected, a progress of the conjugation reaction, and for a quantitative/qualitative analysis of the kinds and the amount of the conjugated materials.

Still another object of the present invention is to provide an evaluation method based on TOF-SIMS for a quantitative/qualitative analysis of the presence or the absence and the amount of a biological material to be detected, in view of quantitative/qualitative analysis of the presence or the absence of conjugation between a biological subject to be detected including proteins, cells, cell extract and nucleotides and nanoparticles on which functional groups that can form a specific conjugation to said biological subject to be detected are formed and the amount of the conjugated material.

Technical Solution

The method for evaluating conjugation between materials using TOF-SIMS according to the present invention is now described in detail herein below. Unless they are defined otherwise, technological terminology and scientific terminology used herein have a meaning that is usually understood by a person skilled in the art. In the following detailed description of the invention and the drawing attached thereto, publicly known function and constitution which may unnecessarily cloud the gist of the present invention are omitted.

Figure 1:
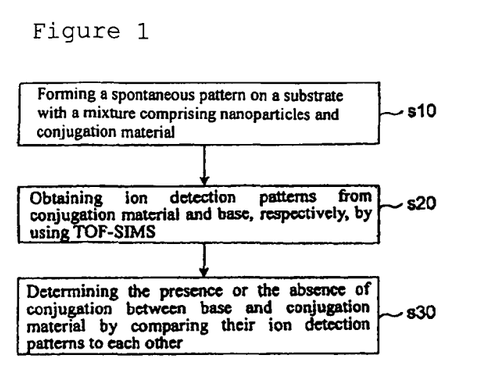
FIG. 1 is an exemplary flow chart showing a procedural flow of the method for evaluating conjugation between materials using TOF-SIMS according to the present invention.

The method of evaluating conjugation between materials using TOF-SIMS according to the present invention is characterized in that it is carried out by following the steps which comprise, a) forming a spontaneous pattern on a substrate with a mixture comprising nanoparticles and a conjugation material selected from organic, bio or inorganic material (i.e., s10 of FIG. 1), b) obtaining an ion detection pattern from said conjugation material and said nanoparticles, respectively, depending on their position on the substrate by using TOF-SIMS (i.e., s20 of FIG. 1), and c) determining whether the conjugation is formed between said conjugation material and said nanoparticles by comparing the ion detection pattern of said conjugation material with the ion detection pattern of said nanoparticles (i.e., s30 of FIG. 1). In the context of the present invention, the above-described conjugation means a chemical or an electric conjugation between two materials.

The above-described ion detection pattern from nanoparticles corresponds to detection intensity of cations or anions of a material comprised in the nanoparticles, depending on their position on substrate (i.e., with position information). The above-described ion detection pattern from conjugation materials corresponds to detection intensity of cations or anions of a material comprised in the conjugation materials, depending on their position on substrate (i.e., with position information).

Said ion detection pattern from nanoparticles is a result obtained from measurement using TOF-SIMS on molecular ion (parent ion), cluster ion or fragment ion of the nanoparticles that are not present in a conjugation material. On the other hand, said ion detection pattern from conjugation material is a result obtained from measurement using TOF-SIMS on molecular ion, cluster ion or fragment ion of a conjugation material that are not present in nanoparticles.

As a result, it is possible to obtain detection intensity of specific ions originating from the nanoparticles which has position information on the substrate (i.e., ion detection pattern of nanoparticles) and detection intensity of specific ions originating from the conjugation material which has position information on the substrate (i.e., ion detection pattern of conjugation material), from above step b) (i.e., s20).

During above step c) (i.e., s30), when said ion detection pattern of nanoparticles and ion detection pattern of conjugation material are found on the same position, it is determined that there is a conjugation between such nanoparticles and conjugation material. In other words, when specific ions of nanoparticles and the other specific ions of conjugation material are detected for the same position information, it is determined that said conjugation material is indeed conjugated to said nanoparticles. However, when only one kind of said ions, i.e., either specific ions of nanoparticles or specific ions of conjugation material are detected for the same position information, it is determined that said conjugation material is not conjugated to said nanoparticles (i.e., non-conjugation).

In this case, said position information can be point position information, one-dimensional position information or two-dimensional position information. From one or two-dimensional position information, when specific ions of the nanoparticles are detected for the position information from which specific ions of the conjugation material are detected, it is determined that the conjugation material is conjugated to the nanoparticles. For all of position information, such determination needs to be carried out.

Position information that is determined as conjugation and other position information that is determined as non-conjugation may exist at the same time.

When position information that is determined as conjugation and other position information that is determined as non-conjugation exist at the same time but specific ions of the conjugation material are detected for all the position information from which said specific ions of the nanoparticles are detected, or specific ions of the nanoparticles are detected for all the position information from which said specific ions of the conjugation material are detected, it is preferable to determine that all of the conjugation materials are conjugated to the nanoparticles, regardless of the number of position information which has been determined as non-conjugation.

When position information that is determined as conjugation and other position information that is determined as non-conjugation exist at the same time but a conjugation level, which is obtained by dividing total number of position information that has been determined as conjugation by total number of position information from which specific ions of the conjugation material are detected is bigger than a certain critical value, it is preferably determined that all of the conjugation materials are conjugated to the nanoparticles. On the other hand, if it is smaller than said critical value, it is preferably determined that there are some conjugation materials that have not been conjugated to the nanoparticles.

When it is found that there are some conjugation materials that have not been conjugated to the nanoparticles, it is preferable that a fraction of the conjugation materials that have been conjugated to the nanoparticles compared to the total weight of the conjugation material is proportional to the value which is obtained by dividing the total number of position information that has been found to be a conjugation by the total number of position information from which specific ions of the conjugation material have been detected.

Therefore, based on the evaluation method of the present invention, the presence or the absence of conjugation between nanoparticles and conjugation materials can be qualitatively determined. Further, conjugation level and total amount of the conjugation material, etc. can be also determined quantitatively.

As explained in the above, the present invention relates to a method for evaluating the presence or the absence of conjugation between two materials based on nanoparticles by using TOF-SIMS. Thus, said conjugation materials can be a bio, organic or inorganic material. Said conjugation materials can also be a complex material of bio-organic, organic-inorganic, or inorganic-inorganic materials. Said conjugation between the conjugation materials and the nanoparticles can be either chemical or electrical conjugation, and it can be a conjugation resulting from a spontaneous or a non-spontaneous reaction. Said mixture is preferably a liquid comprising said nanoparticles and said conjugation materials, and said conjugation materials can be in a state of dispersion or solution.

During the step for forming a pattern on a substrate by using said mixture, the substrate plays a role of supporting the mixture. Any kind of material can be used as a substrate in the present invention, as long as it does not chemically react with said mixture.

For the step for forming a pattern on a substrate by using said mixture, the above-described pattern forming step is a process of spontaneously distributing on a substrate said mixture comprising nanoparticles and conjugation materials. Said distribution (pattern) can be an irregular pattern of the mixture comprising nanoparticles and conjugation materials.

Preferably, ion detection patterns of the conjugation materials and the nanoparticles at said step b) are the results separately measured for the same two-dimensional area on the substrate, and correspond to detection intensity of each ion which carries two-dimensional position information obtained from area scan by TOF-SIMS.

In accordance with such area scan, a conjugation between the nanoparticles and the conjugation materials can be determined for a large area with a single measurement. Further, not only the accuracy for measuring the conjugation is improved but also the presence or the absence of conjugation, the progress of the conjugation, and the progress level of the conjugation can be determined.

To achieve a determination as to whether a conjugation is formed between said conjugation materials and said nanoparticles and a preferred quantitative analysis of the conjugation between them during the above-described step c), it is preferable that an ion detection pattern of the nanoparticles, which is a measurement result from TOF-SIMS, is transformed into a binary pattern; i.e., position information (x, y) showing a detection value for the ions of nanoparticles more than specific critical intensity is transformed value 1, while position information (x, y) showing a detection value less than specific critical intensity is transformed value 0. In addition, it is preferable that an ion detection pattern of the conjugation material, which is a measurement result from TOF-SIMS, is transformed into a binary pattern; i.e., position information (x, y) showing a detection value for the ions of conjugation material more than specific critical intensity is transformed value 1, while position information (x, y) showing a detection value less than specific critical intensity is transformed value 0.

Even when it is transformed into a binary pattern, if the ion detection pattern of the conjugation materials and the ion detection pattern of the nanoparticles have value 1 at the same position information, it is determined that such conjugation materials and nanoparticles are conjugated to each other (i.e., conjugation). However, if they have a value different to each other (i.e., 0, 1 or 1, 0) or both have value 0, it is determined that such conjugation materials and nanoparticles are not conjugated to each other (i.e., non-conjugation).

Even when it is transformed into a binary pattern, if the binary pattern of the conjugation material have value 1 for all of the position information wherein the binary pattern of the nanoparticles has value 1, or the binary pattern of the nanoparticles have value 1 for all of the position information wherein the binary pattern of the conjugation materials have value 1, it is preferable to determine that all of the conjugation materials are conjugated to the nanoparticles, regardless of the number of the position information which has been determined as non-conjugation.

Even when it is transformed into a binary pattern, determination of conjugation or non-conjugation is made for all the position information likewise. When a conjugation level, which is obtained by dividing total number of position information determined to be conjugation by the number of position information from which a specific ion of the conjugation materials has been detected (i.e., total number of position information having value 1 in the binary pattern of the conjugation materials), is more than a specific critical value, it is determined that all of the conjugation materials are conjugated to the nanoparticles. If it is lower than said specific critical value, it is determined that some of the conjugation materials are not conjugated to the nanoparticles.

For a qualitative and quantitative analysis on conjugation, steps as follows are carried out, similar to those before the transformation into a binary pattern: calculating a reference, which is the total number of position information having value 1 on binary pattern of the nanoparticle ions; calculating a conjugation amount, which is the total number of position information wherein both the binary pattern of the ions of the nanoparticle and the binary pattern of the ions of the conjugation materials have value 1 at the same position information; and calculating a conjugation level which indicates a degree of conjugation of the conjugation materials to the nanoparticles, by dividing said conjugation amount by said reference. As a result, based on said conjugation level obtained by dividing said conjugation amount by said reference, the amount or the concentration of the conjugation materials can be obtained.

Furthermore, by carrying out several steps as follows, the amount of the conjugation materials that are conjugated to the nanoparticles and the amount of the conjugation materials that are not conjugated to the nanoparticles can be obtained: calculating a total amount, which is the total number of position information having value 1 on binary pattern of the ions of the conjugation material; calculating a conjugation amount, which is the total number of position information in which both the binary pattern of the ions of the conjugation material and the binary pattern of the ions of the nanoparticles have value 1 at the same position information; and calculating a conjugation level which indicates the degree of conjugation of the conjugation materials to the nanoparticles, by dividing said conjugation amount by said total amount.

According to the determination method of the present invention, an evaluation mistake due to measurement error and characteristic of materials can be prevented and a qualitative analysis based on intuition can be made. It is preferable that the above-mentioned quantitative analysis is also carried out by using the images of the above-described ion detection patterns, if possible. Specifically, it is preferable that, said ion detection patterns are individually transformed into an image and then by overlapping such images the presence or the absence of conjugation between the nanoparticles and the conjugation materials and the conjugation amount are analyzed both quantitatively and qualitatively.

Figure 2:
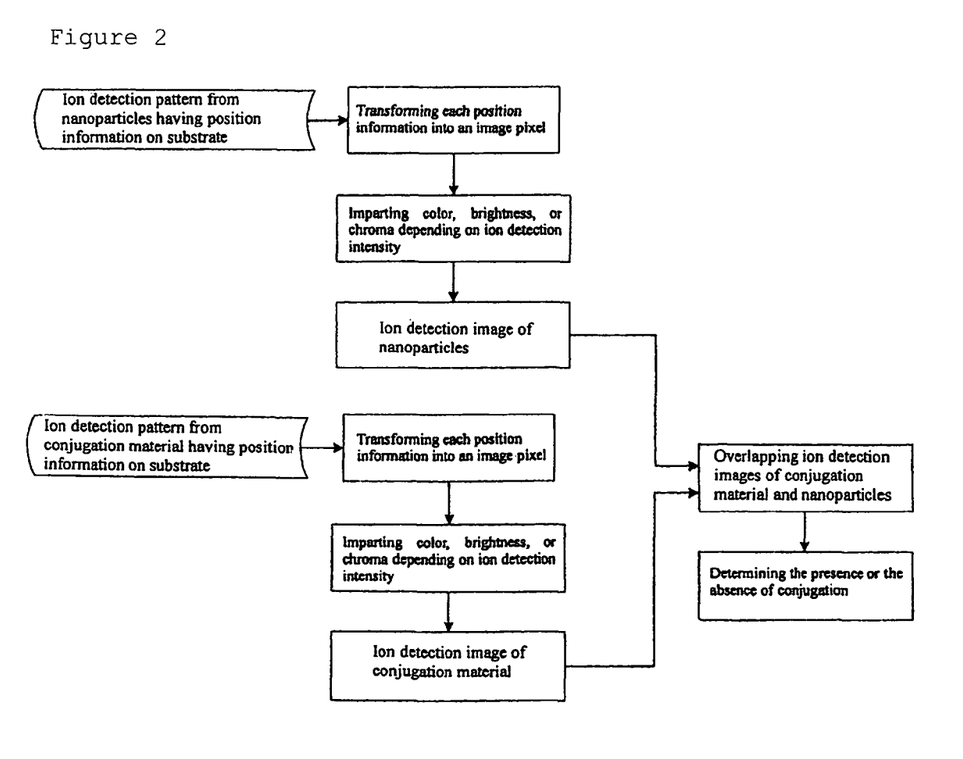
FIG. 2 is an exemplary flow chart showing a procedural flow of the method for evaluating conjugation between materials using TOF-SIMS, especially the evaluation based on transformation of ion detection pattern into an image, according to the present invention.

As it is illustrated in FIG. 2, in order to determine qualitatively the presence or the absence of conjugation between the nanoparticles and the conjugation materials, the above described step c) is preferably carried out by following the steps as follows: transforming the above-described position information into an image pixel, and; imparting color, brightness, chroma, or a combination thereof to said pixel depending on ion intensity based on said position information, thus resulting a transformation of each ion detection pattern of the nanoparticles and the conjugation materials into an ion detection image of the nanoparticles and an ion detection image of the conjugation materials, respectively. When the ion detection image of the nanoparticles and the ion detection image of the conjugation materials are overlapped to each other, it is preferably determined that said conjugation materials are conjugated to said nanoparticles.

In this case, when said ion detection image of the nanoparticles is completely overlapped with said ion detection image of the conjugation materials or said ion detection image of the conjugation materials is completely overlapped with said ion detection image of the nanoparticles, it is preferably determined that all of said conjugation materials are conjugated to said nanoparticles.

In this case, when there is a region in which said ion detection image of the conjugation materials and said ion detection image of the nanoparticles are not overlapped to each other, but the area overlapped with said ion detection image of the conjugation materials is divided based on total area of said ion detection image of the nanoparticles (i.e., total pixel area in which ions of nanoparticle are detected so that color, brightness, chroma or a combination thereof are imparted thereto) is more than a specific critical value, it is preferably determined that all of the conjugation materials are conjugated to the nanoparticles.

In this case, when there is a region in which said ion detection image of the conjugation materials and said ion detection image of the nanoparticles are not overlapped to each other, but the area overlapped with said ion detection image of the nanoparticles is divided based on total area of said ion detection image of the conjugation materials (i.e., total pixel area in which ions of conjugation material are detected so that color, brightness, chroma or a combination thereof are imparted thereto) is more than a specific critical value, it is preferably determined that all of the conjugation materials are conjugated to the nanoparticles.

Even when it is transformed into an image, a quantitative analysis on the presence or the absence of conjugation can be made. In this case, the conjugation level which is obtained by dividing the above-described conjugation amount by the above-described reference corresponds to a value obtained from dividing the above-described overlapped area by the above-described total area of the ion detection image of the nanoparticles, and the conjugation level which is obtained by dividing the above-described conjugation amount by the above-described total amount corresponds to a value obtained from dividing the above-described overlapped area by the above-descried total area of the ion detection image of the detection materials.

In addition, after a binary pattern is formed from an ion detection pattern as explained above, an imaging of the binary pattern can be obviously carried out to determine the presence or the absence of conjugation and to achieve a quantitative/qualitative analysis on conjugation amount, etc., by using the resulting images.

Figure 3:
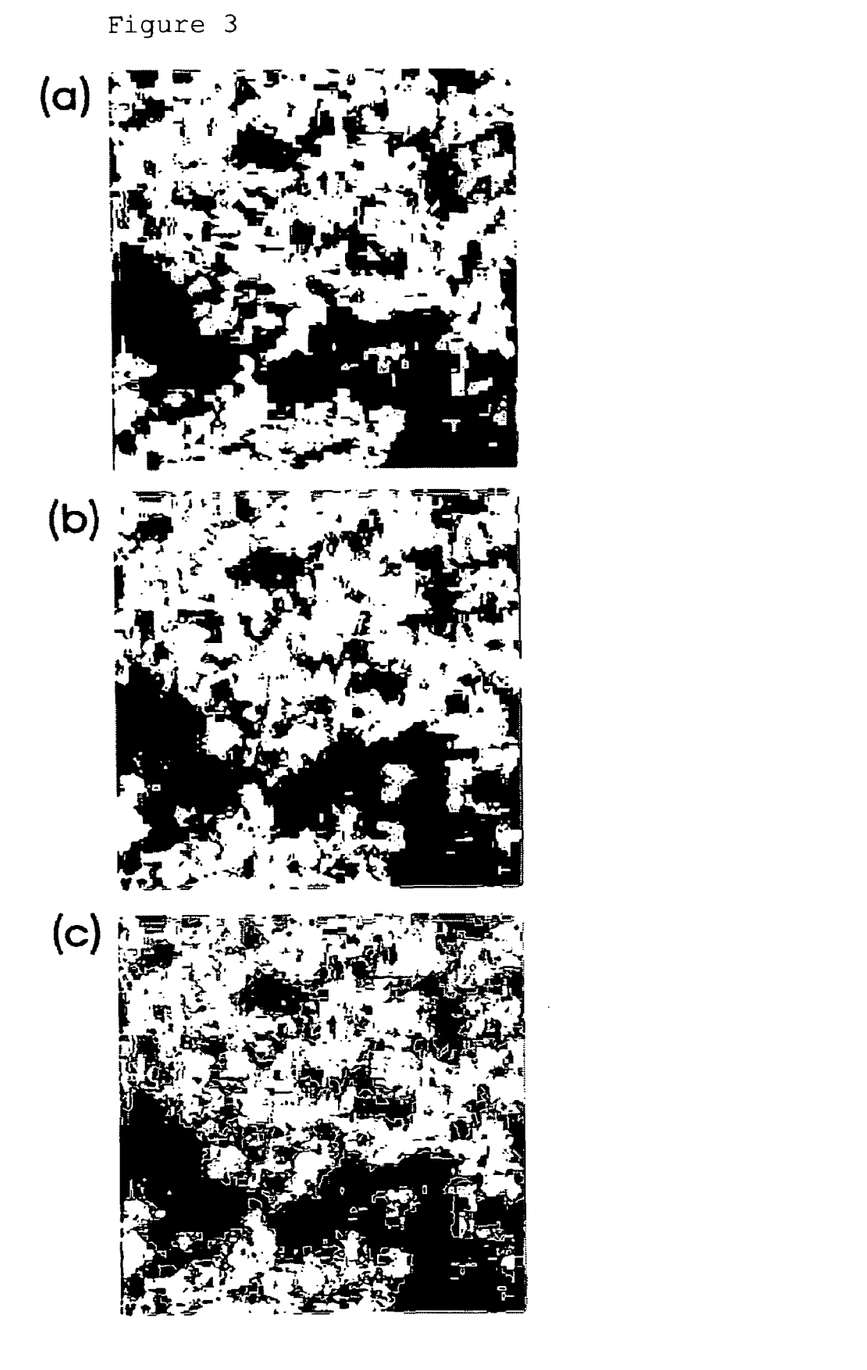
FIG. 3 shows an example of evaluating conjugation between materials using TOF-SIMS according to the present invention, in which the evaluation is based on the transformation into a binary pattern and then into an image.

FIG. 3 shows one example of the evaluation method of the present invention, wherein an ion detection pattern having two-dimensional position information is transformed into a binary pattern, which is then transformed into a corresponding image. Specifically, FIG. 3(a) is a binary pattern image of nanoparticle ions and FIG. 3(b) is a binary pattern image of conjugation material ions, wherein white color is given to a pixel having value 1 while black color is given to a pixel having value 0, each pixel corresponding to specific position information. FIG. 3(c) is an image that is obtained by overlapping said FIG. 3(a) and FIG. 3(b). White area can occur only when the images from two ion detection patterns are overlapped to each other. Black area in FIG. 3(c) indicates that all of the corresponding pixels have value 0, and gray area in FIG. 3(c) indicates that all of the corresponding pixels have value 0 and 1, or 1 and 0. In other words, for the area in which only one kind of the ions of the nanoparticles or the ions of the conjugation material are detected, gray color is shown.

If the white area of FIG. 3(c) is divided by the white area of FIG. 3(b), the conjugation level, which indicates the amount of the conjugation materials that are conjugated to the nanoparticles compared to their total amount, can be obtained.

In this case, as it has been described in detail above, when said conjugation level is greater than specific value, an error coming from experimental measurements, and an error due to a difference in parameters of materials such as an amount of secondary ions generated according to the same injection energy between the nanoparticles and the conjugation materials and scattering level, etc. are considered, and it is consequently determined that all of the conjugation materials are conjugated to the nanoparticles.

When the white area of FIG. 3(c) is divided by the white area of FIG. 3(a), information about the amount or the concentration of the conjugation materials can be obtained. This method which can be used to obtain information about the amount or the concentration of the conjugation materials is preferably carried out after all of the conjugation materials are determined to be conjugated to the nanoparticles.

The nanoparticles are preferably nanoparticles comprising quantum dots.

The conjugation materials have a thiol group and are preferably bi-functional materials in that they additionally have one more functional group selected from carboxyl group, hydroxyl group and amino group.

The conjugation materials are preferably an antibody or a nucleotide.

Based on a method of evaluating conjugation between materials using TOF-SIMS of the present invention, conjugation of a specific functional group including ligands to specific nanoparticles, nanolines or nanorods can be analyzed both quantitatively and qualitatively. Furthermore, conjugation process can be also analyzed.

Therefore, a quantitative and qualitative analysis on multi-step conjugation and substitution carried out for forming functional groups which can specifically conjugate to a biological analyte such as specific antibody, cell, protein extract and nucleotide, etc. on said nanoparticles, nanolines or nanorods, is possible. In addition, detailed information about conjugation process for each step of multiple conjugation and substitution can be obtained. For such multi-step conjugation and substitution, two materials which conjugated to each other in single step can be a conjugation material and a nanoparticle, respectively, and a material having a completed conjugation during previous step can be a nanoparticle.

By using the inventive method of evaluating conjugation between materials using TOF-SIMS, the presence or the absence of an antibody, a cell, or a nucleotide can be determined and their quantitative analysis can be also carried out. For such determination, said conjugation materials are preferably an antibody, a cell, or a nucleotide and on their surface the nanoparticles preferably have functional groups that can specifically conjugate to said antibody or cell or functional groups that can complementarily conjugate to said nucleotide.

In this case, it is preferable that the ion detection pattern of nanoparticles is the ion detection pattern of said functional groups. Similar to a transformation of said ion detection pattern of nanoparticles into a binary pattern described above, said ion detection pattern of the functional groups can be transformed into a binary pattern; i.e., position information (x, y) from which the ions of the functional groups have been detected with an intensity more than a specific critical intensity is given value 1, and position information having a detection intensity less than a specific critical intensity is given value 0.

Similarly, ion detection pattern of an antibody, a cell or a nucleotide can be also transformed into a binary pattern; i.e., position information (x, y) from which the ions of the conjugation materials have been detected with an intensity more than a specific critical intensity is given value 1, and position information having a detection intensity less than a specific critical intensity is given value 0.

For the above-described quantitative analysis of an antibody, a cell or a nucleotide, several steps as follows are carried out: calculating a reference, which is the total number of position information having value 1 on binary pattern of the ions of the functional group; calculating a conjugation amount, which is the total number of position information wherein both the binary pattern of the ions of the functional group and the binary pattern of the ions of the conjugation materials have value 1 at the same position information, and; calculating a conjugation level, which indicates a degree of conjugation of the conjugation materials to the functional groups, by dividing said conjugation amount by said reference.

When said conjugation amount is 0, it is found that an antibody, a cell or a nucleotide are not present. On the other hand, when said conjugation amount is more than 0, it is found that an antibody, a cell or a nucleotide are present. In addition, from said conjugation level, the amount of an antibody, a cell or a nucleotide can be determined.

Even when it is not transformed into a binary pattern, qualitative and quantitative analysis of an antibody, a cell or a nucleotide can be carried out, by using the number of position information from which ions of the nanoparticle are detected, the number of position information from which ions of the detection materials are detected, and the number of position information from which both the ions of the nanoparticle and the ions of the detection materials are detected, similar to those described above. Further, the presence or the absence of said antibody, cell or nucleotide can be qualitatively determined based on a transformation into an image, similar to those described above. Sill further, amount of said antibody, cell or nucleotide can be determined based on an area of overlapped image, similar to those described above.

The above-described quantitative and qualitative analysis at step c) can be accomplished by using a typical digital signal processor (DSP). Parameter information such as specific critical intensity for said transformation into binary pattern and specific critical value that can be ignored as an experimental error, etc., all required for an efficient implementation of the evaluation method of the present invention, can be stored in a memory and used later after being loaded into said DSP, if necessary. In this case, each parameter stored in memory is an optimized value which may vary depending on kinds of the nanoparticles and the conjugation materials and measurement condition for TOF-SIMS, etc. Quantitative and qualitative results of determination about the presence or the absence of conjugation and the conjugation level, etc. can be expressed on a general display device that is connected to said DSP. When image transformation is carried out, respective images and a resulting overlapped image can be also expressed on said general display device.

Effect of the Invention

The method for evaluating conjugation between two materials using TOF-SIMS according to the present invention can be used for determining whether the conjugation is formed between organic and bio materials, organic and inorganic materials, inorganic and inorganic materials, or organic and organic materials, based on nanoparticles. Further, conjugation level and an amount of conjugated material can be determined both quantitatively and qualitatively, and progress for forming a conjugation can be also determined. Most of all, when a multi-step conjugation and substitution are involved, the presence or the absence of conjugation (or substitution) of a specific material and an identity of a material which has been conjugated (or substituted) can be determined at each step, and conjugation between two materials can be evaluated in accordance with their spatial distribution.

The evaluation method of the present invention provides a means for carrying out basic studies on conjugation between materials that are present on nanoparticles. In addition, it can be applied for manufacturing a bio-organic-inorganic complex to detect a specific biological material and for a sensor's detection step to detect a specific biological material.

When applied for a sensor's detection step, the evaluation method of the present invention will be useful for a quantitative determination of the presence and the amount of a specific biological material, rather than relying on signal detection based on electric/magnetic signals coming from a conjugation to specific biological materials. In addition, according to the method of the present invention, the conjugated materials can be differentiated from non-conjugated materials that remain as residuals.

In particular, the method of the present invention is advantageous in that, ligands or biological materials conjugated to nanoparticles including quantum dots can be analyzed and evaluated without any labeling, large-area analysis and evaluation are possible even with a single measurement, and information on spatial distribution of the ligands or biological materials that are conjugated to nanoparticles can be obtained.

BRIEF DESCRIPTION OF DRAWINGS

FIG. 3(a) is a binary pattern image of ions of nanoparticles. FIG. 3(b) is a binary pattern image of conjugation materials. FIG. 3(c) is an overlay of FIG. 3(a) and FIG. 3(b).

FIG. 4(a) shows TOF-SIMS image of ZnSCdSe$^-$ that had been obtained by transformation of the ZnSCdSe$^-$ detection pattern of CdSe—ZnS quantum dots into TOF-SIMS image. FIG. 4(b) shows TOF-SIMS image of the stearate salts that had been obtained by transformation of the detection pattern of stearate salt anions into TOF-SIMS image, wherein the stearate salt is one of the organic materials used for preparing CdSe—ZnS quantum dots. FIG. 4(c) is an overlay of FIG. 4(a) and FIG. 4(b).

FIG. 5(a) shows TOF-SIMS image of ZnS⁻ that had been obtained by transformation of the ZnS⁻ detection pattern into TOF-SIMS image. FIG. 5(b) shows TOF-SIMS image of Zn·MPA-H⁻ that had been obtained by transformation of the Zn·MPA-H⁻ detection pattern into TOF-SIMS image. FIG. 5(c) shows TOF-SIMS image of the stearate salts that had been obtained by transformation of the detection pattern of stearate salt anions into TOF-SIMS image. FIG. 5(d) is an overlay of FIG. 5(a) showing TOF-SIMS image of ZnS⁻ and FIG. 5(c) showing the TOF-SIMS of the stearate salts.

FIG. 6(a) shows TOF-SIMS image of Se⁻ that had been obtained by transformation of the Se⁻ detection pattern into TOF-SIMS image. FIG. 6(b) shows TOF-SIMS image of phosphate salts ($PO_3^-$) that had been obtained by transformation of the $PO_3^-$ detection pattern into TOF-SIMS image. FIG. 6(c) shows TOF-SIMS image of thymine base (Thy-H⁻) that had been obtained by transformation of the Thy-H⁻ detection pattern into TOF-SIMS image. FIG. 6(d) shows TOF-SIMS image of the stearate salts that had been obtained by transformation of the detection pattern of stearate salt anions into TOF-SIMS image.

BEST MODE FOR CARRYING OUT THE INVENTION

In view of the following examples, the method for evaluating conjugation between materials using TOF-SIMS according to the present invention will be explained in detail. The following examples are given to fully explain the spirit of the present invention to a person skilled in the art. Thus, the present invention is not limited to the following examples. Rather, it can be embodied in other various forms and many variations and modifications of the present invention will be evident to a person having ordinary knowledge in the pertinent art.

CdSe—ZnS core-shell quantum dots comprising CdSe core and ZnS shell were produced and by using TOF-SIMS the formation of a core-shell between CdSe and ZnS in CdSe—ZnS core-shell quantum dots (i.e., conjugation between CdSe and ZnS) was determined and evaluated. In addition, the presence or the absence of organic ligand which can be produced during the manufacturing process of CdSe—ZnS core-shell quantum dots and conjugation between them were determined and evaluated.

In order to produce CdSe quantum dots, CdO (4 mmol), stearic acid (8 mmol) and octylamine (5 mL) were added to 1-octadodecine (ODE; 5 mL), and heated to 250°. When the solution became transparent, the temperature was lowered to 130° and 1-octadodecine was further added to the solution to obtain a total volume of 50 mL. Then, 200-mesh Se powder (2 mmol) was added thereto and the temperature was raised to 240° with a heating rate of 25-30° per minute. It was found that CdSe is formed at approximately 210° at which point Se starts to dissolve. With said octylamine, the size of nanoparticles was adjusted. The resulting CdSe quantum dots were purified several times using a methanol solution comprising propylamine to remove residual stearate salts, and stored in hexane.

In order to prepare CdSe/ZnS, purified CdSe quantum dots having wurtzite structure (about 0.1~0.3 μmol, i.e., 10 mg) were added into a mixture solution comprising 1-octadodecine (2 mL) and octadecylamine (ODA; 4 g) and dispersed in the mixture. The resulting solution was heated to 190° with vigorous stirring. While raising the temperature of the solution of CdSe quantum dots to 190~210°, Zn stock solution (0.05M) and a sulphur stock solution (0.05M) were added dropwise thereto. Said 0.05M Zn stock was prepared by mixing 1-octadodecine solution and oleic acid at about 240°, and said 0.05M sulphur stock solution was prepared by dissolving sulphur powder in 1-octadodecine. By adding the Zn stock solution and the sulphur stock solution, quantum dots having CdSe—ZnS core-shell structure wherein CdSe core quantum dots are coated with ZnS shell (about 3 ml) were prepared. The resulting quantum dots having CdSe—ZnS core-shell structure were purified with methanol.

In order to carry out an analysis by TOF-SIMS, CdSe—ZnS quantum dots in colloid state was applied to Si substrate (100), which had been previously cleaned in piranha solution, and dried under vacuum.

As a measurement condition for TOF-SIMS, TOF-SIMS V (ION-TOF GmbH, Germany) apparatus and 25 keV Bi+ ion gun were used. The ion gun was operated at 5 kHz, and an average ionic current which had been measured using Faraday cup was 0.2 pA (Bi+) in an earthed sample holder. Pulse duration time from a bunching system was 10.9 ns, allowing a mass resolution (M/□M) more than 8000 at negative mode. The raster area formed by first ions was 200×200 μm² and the ion amount was maintained within $10^{12}$ ions·cm⁻². Measurements were carried out at negative mode and the spectrum of anions was essentially calibrated by having peaks of C⁻, CH⁻, $C_2H^-$, $C_4H^-$ as reference. Spatial resolution, which serves as a gap between position information, was 1.5 μm and the measured anion spectrum was converted to an image with 256×256 pixels, having a unit pixel of 1.5 μm. Black color shown in an image indicates that corresponding anions were not detected. Stronger the detection intensity of anions, it has a higher brightness.

Figure 4:
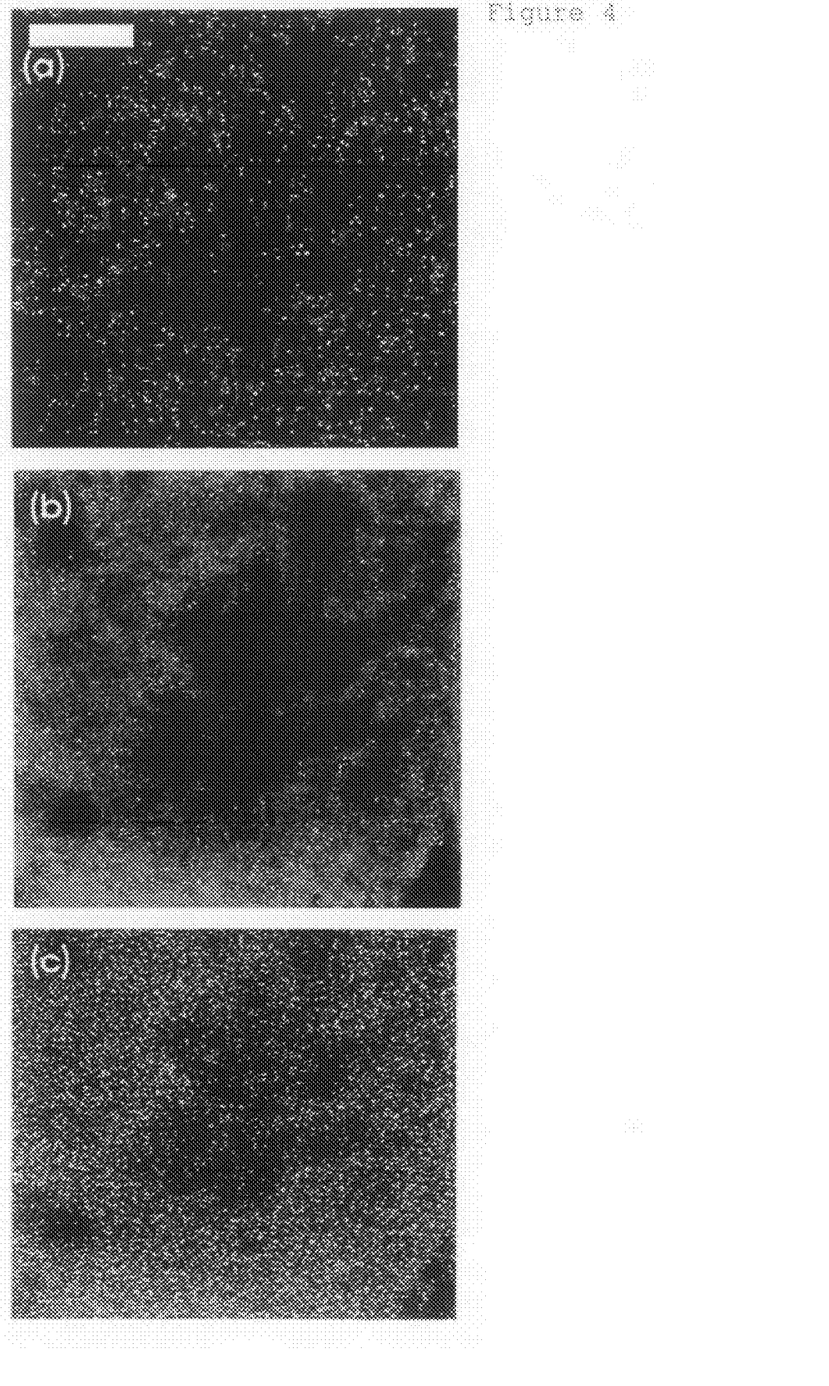
FIG. 4 shows an example of evaluating conjugation between ligands and CdSe—ZnS quantum dots.

FIG. 4 (a) shows ZnSCdSe⁻ TOF-SIMS image of CdSe—ZnS quantum dots that had been produced on Si substrate (100) in the above. As it can be seen from FIG. 4(a), ZnS—CdSe quantum dots were produced and an irregular pattern was formed on the Si substrate by ZnS—CdSe quantum dots. FIG. 4(b) shows a TOF-SIMS image of stearate salts (m/z 283) as an organic compound used for preparing CdSe—ZnS quantum dots in the above. According to an overlay image of FIG. 4(c) (i.e., overlay of FIG. 4(a) and FIG. 4(b)), it is found that the TOF-SIMS image of CdSe—ZnS quantum dots is completely overlapped with the TOF-SIMS image of the stearate salts. Thus, it is considered that to the CdSe—ZnS quantum dots prepared above the stearate salts are conjugated as a ligand.

Based on the results shown in FIG. 4, it was found that CdSe—ZnS quantum dots were prepared and the stearate salts as a ligand were conjugated to the surface of the quantum dots. Then, ligand substitution on the above-prepared quantum dots was carried out.

To carry out ligand substitution, 20 mg of CdSe—ZnS quantum dots to which stearate salts are conjugated were dissolved in anhydrous methanol (10 mL) comprising 10 μL 3-mercaptopropionic acid (hereinafter, MPA) and pH was adjusted to 10 using tetramethylammonium hydroxide. Thereafter, Ar gas was purged with stirring at 60° for 2 hours until the color of the solution became magenta. 40 mL of ethyl acetate was added and the solution was centrifuged at 4000 rpm for 5 min to recover the quantum dots. The recovered quantum dots were washed with ethyl acetate and dried under vacuum. Said washing was carried out more than three times. The ethyl acetate solution comprising the washed and dried quantum dots was applied to Si substrate (100), which had been pre-cleaned in piranha solution, and then dried under vacuum.

FIG. 5(a) shows TOF-SIMS image of ZnS⁻. From FIG. 5(a), it is acknowledged that the quantum dots form an irregular pattern on the silicone substrate. FIG. 5(b) shows TOF-SIMS image Zn·MPA-H⁻. Based on the fact that the image of FIG. 5(b) is completely overlapped with the image of FIG. 5(a), it is found that all of MPAs are conjugated to the quantum dots. This is in good agreement of FIG. 5(b) which shows a detection of Zn·MPA-H⁻ ions that are secondary ions resulting from conjugation of MPAs to the surface of the quantum dots. Consequently, it is determined that with the ligand substitution described above the stearate salts were substituted by MPAs having carboxy (—COOH) groups.

Figure 5:
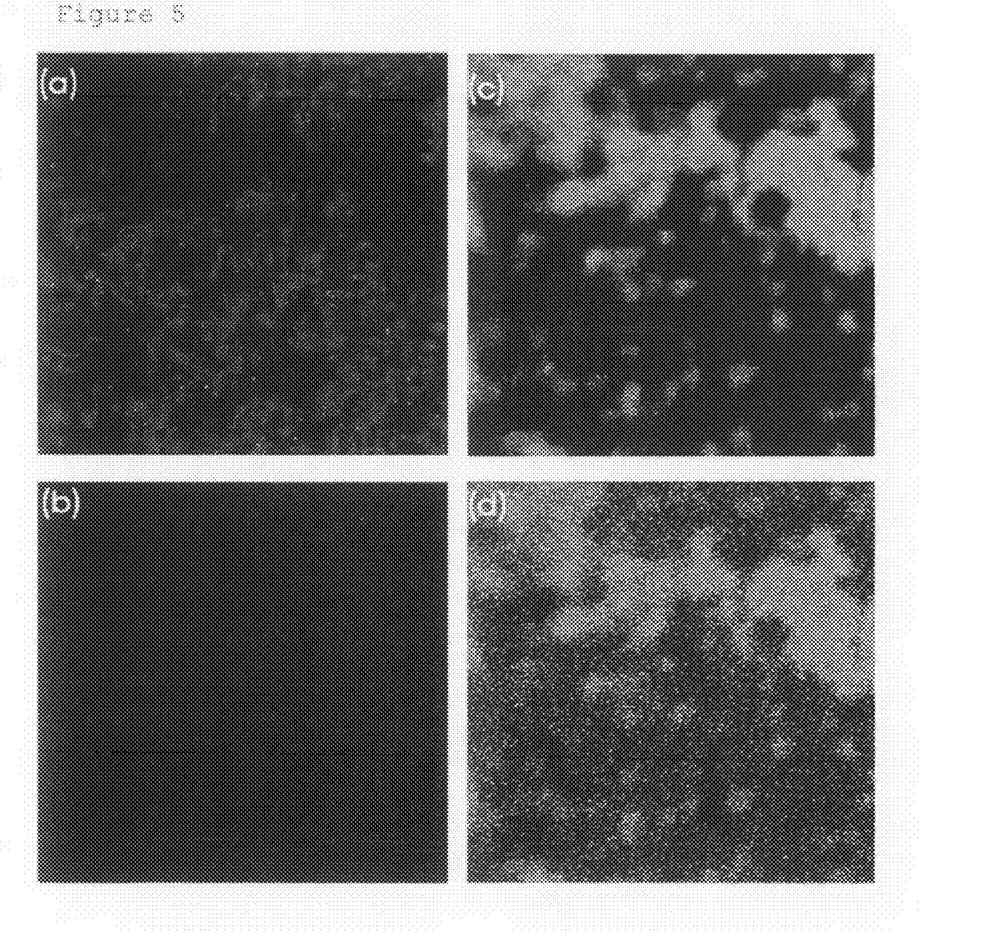
FIG. 5 shows an example of evaluating conjugation after the ligand substitution of the stearate salts conjugated to the CdSe—ZnS quantum dots with 3-mercaptopropionic acid (MPA).

Further, to determine the conjugation of the stearate salts which had been conjugated to the quantum dots before ligand substitution, TOF-SIMS image of the stearate salts was obtained. As a result, it was found that for the region wherein none of the quantum dots and MPAs was detected, i.e., a substrate region, the stearate salts remained as it is shown in FIG. 5 (c). In addition, according to an overlay image of FIG. 5(d) which is obtained by overlapping TOF-SIMS image of ZnS and TOF-SIMS image of the stearate salts, it was determined that the stearate salts were not conjugated to the quantum dots. Based on these results, it was found that, even after the ligand substitution and washing more than three times the stearate salts remained in the ethyl acetate solution.

For said ligand substitution, by using 3-mercaptopropanol (hereinafter, MPO) or 2-aminoethanethiol (hereinafter, AET) instead of MPA, ligand substitution of the stearate salts using MPO having hydroxyl group (—OH) or AET having amine group (—NH$_2$) was carried out, similar to the substitution using MPA. As a result of TOF-SIMS measurement and analysis, it was found that all of the TOF-SIMS patterns of the quantum dots are overlapped with the TOF-SIMS of M0PO-H⁻ or AET-H⁻, similar to the ligand substitution using MPA. The stearate salts were not conjugated to the quantum dots and remained only on the substrate.

As it is described in the above, quantum dots capped with MPA were prepared based on ligand substitution between MPA and stearate salts. In addition, to said MPA-capped quantum dots a DNA aptamer which can be further conjugated to thrombin was conjugated.

To carry out said reaction, MPA-capped quantum dots (1 nmol) was dissolved in PBS buffer (pH 5.4) and the carboxy group of the MPA-capped quantum dots was activated by a conversion into N-hydroxysulfosuccinimide (Sulfo-NHS) esters capable of amine reaction, by adding 0.15 mg of 1-ethyl-3-[3-dimethylaminopropyl]carbodiimide hydrochloride (EDC) and 0.21 mg of N-N-hydroxysulfosuccinimide (Sulfo-NHS) to the MPA-capped quantum dots and mixing the resultant for 15 minutes at room temperature. Thrombin-binding aptamer DNA (5'-TTCACTGTGGTTGGTGTGGT-TGG-3'; 5 nmol) was added to the solution comprising activated quantum dots and incubated in β-mercaptoethanol solution (0.5 μl) for two hours at room temperature. After the completion of the incubation, 0.5 mg of N-hydroxylamine hydrochloride was added to prepare quantum dots having DNA aptamer conjugated thereto.

The solution comprising the DNA aptamer-conjugated quantum dots was applied to Si substrate (100), which had been previously cleaned in piranha solution, and then dried under vacuum.

Figure 6:
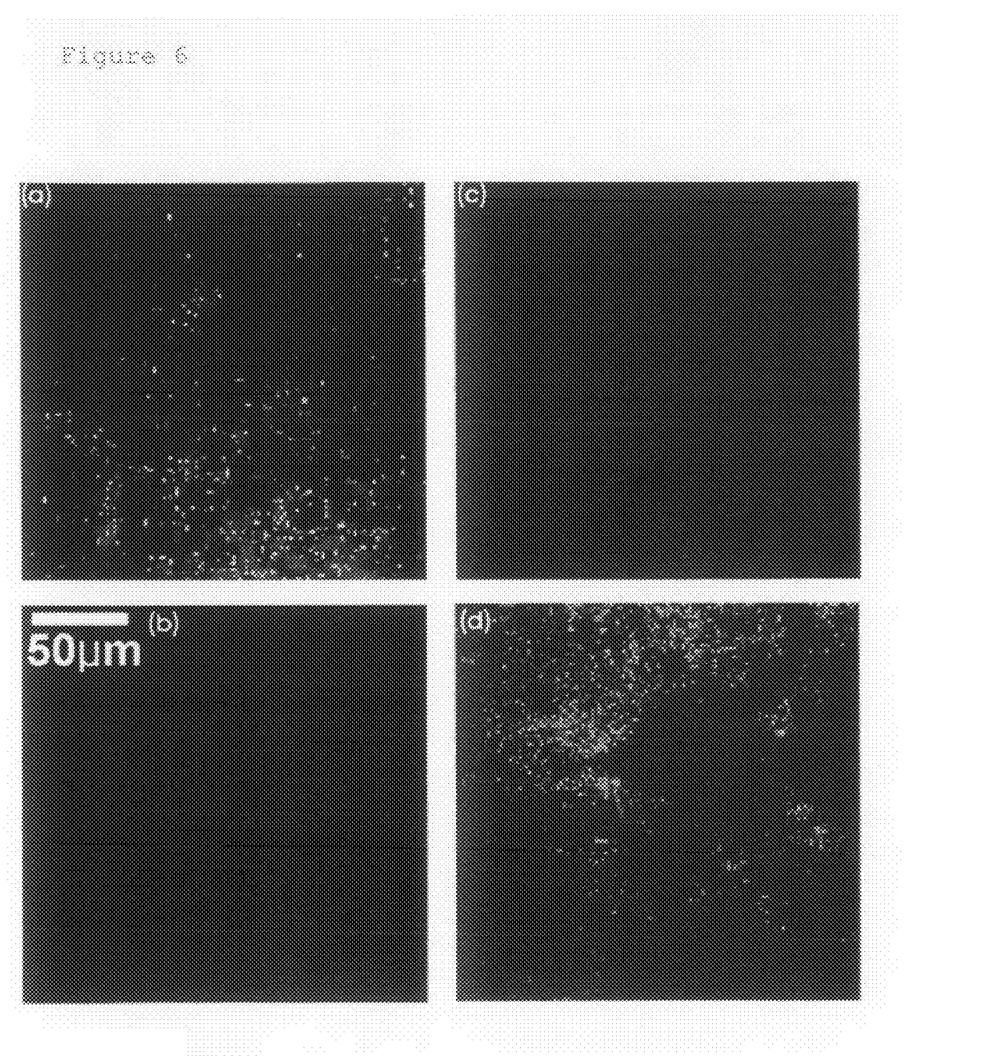
FIG. 6 shows an example of evaluating conjugation between CdSe—ZnS quantum dots capped with MPA by MPA ligand substitution and DNA aptamer.

FIG. 6(a) shows TOF-SIMS image of Se⁻. It is found that the quantum dots form an irregular pattern on the silicone substrate. FIG. 6(b) shows TOF-SIMS image of phosphate salts (PO$_3$⁻) and FIG. 6(c) shows a TOF-SIMS image of thymine base (Thy-H⁻). The quantum dot image pattern of FIG. 6(a) is in complete match of the patterns obtained from phosphate salts or thymine base. Thus, it is determined that the DNA aptamer which can conjugate to thrombin was conjugated to the CdSe—ZnS quantum dots. FIG. 6(d) shows a TOF-SIMS image of the stearate salts. It is determined that the stearate salts remains in the substrate region wherein patterns of thymine, phosphate or the quantum dots were not found.

The invention claimed is:

1. A method of evaluating conjugation between materials using TOF-SIMS (Time-Of-Flight Secondary Ion Mass Spectrometry) comprising the steps of: a) forming a spontaneous pattern on a substrate with a mixture comprising nanoparticles and a conjugation material selected from organic, bio or inorganic material; b) obtaining an ion detection pattern from said conjugation material and said nanoparticles, respectively, depending on their position on the substrate by using TOF-SIMS; and c) determining whether the conjugation is formed between said conjugation material and said nanoparticles by comparing the ion detection pattern of said conjugation material with the ion detection pattern of said nanoparticles.

2. The method of evaluating conjugation between materials using TOF-SIMS of claim 1, wherein the ion detection patterns of the conjugation materials and the nanoparticles at said step b) are separately measured for the same area on the substrate, and correspond to intensity of each ion which carries two-dimensional position information obtained from area scan by TOF-SIMS.

3. The method of evaluating conjugation between materials using TOF-SIMS of claim 2, wherein the ion detection pattern of said nanoparticles is a binary pattern, i.e., position information (x, y) showing a detection value for the ions of nanoparticles more than specific critical intensity is transformed value 1, while position information (x, y) showing a detection value less than specific critical intensity is transformed value 0; and the ion detection pattern of said conjugation material is a binary pattern, i.e., position information (x, y) showing a detection value for the ions of conjugation material more than specific critical intensity is transformed value 1, while position information (x, y) showing a detection value less than specific critical intensity is transformed value 0.

4. The method of evaluating conjugation between materials using TOF-SIMS of claim 1, wherein it is determined that such conjugation materials and nanoparticles are conjugated to each other when the ion detection pattern of said conjugation materials and the ion detection pattern of said nanoparticles are present at the same position.

5. The method of evaluating conjugation between materials using TOF-SIMS of claim 3, wherein said method comprises the steps of: calculating a reference, which is the total number of position information having value 1 on binary pattern of said nanoparticle ions; calculating a conjugation amount, which is the total number of position information wherein both the binary pattern of the ions of said nanoparticle and the binary pattern of the ions of said conjugation materials have value 1 at the same position information; and calculating a conjugation level which indicates a degree of conjugation of said conjugation materials to said nanoparticles, by dividing said conjugation amount by said reference.

6. The method of evaluating conjugation between materials using TOF-SIMS of claim 3, wherein said method comprises the steps of: calculating a total amount, which is the total number of position information having value 1 on binary pattern of the ions of said conjugation material; calculating a conjugation amount, which is the total number of position information in which both the binary pattern of the ions of said conjugation material and the binary pattern of the ions of said nanoparticles have value 1 at the same position information; and calculating a conjugation level which indicates the degree of conjugation of said conjugation materials to said nanoparticles, by dividing said conjugation amount by said total amount.

7. The method of evaluating conjugation between materials using TOF-SIMS of claim 2, wherein said step c) is carried out by the steps of: transforming said position information into an image pixel; and imparting color, brightness or chroma to said pixel depending on ion intensity based on said position information, thus resulting a transformation of each ion detection pattern of said nanoparticles and said conjugation materials into an ion detection image of the nanoparticles and an ion detection image of the conjugation materials respectively, and when the ion detection image of said nanoparticles and the ion detection image of said conjugation materials are overlapped to each other, it is determined that said conjugation materials are conjugated to said nanoparticles.

8. The method of evaluating conjugation between materials using TOF-SIMS of claim 1, wherein said conjugation materials have a thiol group and additionally have one more functional group selected from carboxyl group, hydroxyl group and amino group.

9. The method of evaluating conjugation between materials using TOF-SIMS of claim 1, wherein said conjugation materials are an antibody or a nucleotide.

10. The method of evaluating conjugation between materials using TOF-SIMS of claim 2, wherein said conjugation materials are an antibody, a cell, or a nucleotide and on their surface the nanoparticles have functional groups that can specifically conjugate to said antibody or cell or functional groups that can complementarily conjugate to said nucleotide.

11. The method of evaluating conjugation between materials using TOF-SIMS of claim 10, wherein the ion detection pattern of said nanoparticles is the ion detection pattern of said functional groups.

12. The method of evaluating conjugation between materials using TOF-SIMS of claim 11, wherein the ion detection pattern of said functional groups is a binary pattern, i.e., position information (x, y) from which the ions of the functional groups have been detected with an intensity more than a specific critical intensity is given value 1, and position information having a detection intensity less than a specific critical intensity is given value 0; the ion detection pattern of said conjugation materials is a binary pattern, i.e., position information (x, y) from which the ions of the conjugation materials have been detected with an intensity more than a specific critical intensity is given value 1, and position information having a detection intensity less than a specific critical intensity is given value 0.

13. The method of evaluating conjugation between materials using TOF-SIMS of claim 12, wherein said method comprises the steps of: calculating a reference, which is the total number of position information having value 1 on binary pattern of the ions of said functional group; calculating a conjugation amount, which is the total number of position information wherein both the binary pattern of the ions of said functional group and the binary pattern of the ions of said conjugation materials have value 1 at the same position information; and calculating a conjugation level, which indicates a degree of conjugation of said conjugation materials to said functional groups, by dividing said conjugation amount by said reference.

14. The method of evaluating conjugation between materials using TOF-SIMS of claim 2, wherein it is determined that such conjugation materials and nanoparticles are conjugated to each other when the ion detection pattern of said conjugation materials and the ion detection pattern of said nanoparticles are present at the same position.

15. The method of evaluating conjugation between materials using TOF-SIMS of claim 3, wherein it is determined that such conjugation materials and nanoparticles are conjugated to each other when the ion detection pattern of said conjugation materials and the ion detection pattern of said nanoparticles are present at the same position.

* * * * *